United States Patent [19]

Dimeff

[11] 4,204,326
[45] May 27, 1980

[54] DEVICE FOR RECORDING AND REPRODUCING MANDIBULAR MOTION

[76] Inventor: John Dimeff, 5346 Greenside Dr., San Jose, Calif. 95127

[21] Appl. No.: 965,749

[22] Filed: Dec. 4, 1978

[51] Int. Cl.² .......................... A61C 11/00; A61C 9/00
[52] U.S. Cl. .......................................... 433/50; 433/71
[58] Field of Search .......................... 32/19, 20, 21, 32

[56] References Cited

U.S. PATENT DOCUMENTS

| | | | |
|---|---|---|---|
| 2,043,394 | 6/1936 | Reith | 32/32 |
| 4,034,475 | 7/1977 | Lee | 32/21 |
| 4,111,085 | 9/1978 | Johnson | 83/1 |

*Primary Examiner*—Louis G. Mancene
*Assistant Examiner*—Michael J. Foycik, Jr.

*Attorney, Agent, or Firm*—Limbach, Limbach & Sutton

[57] ABSTRACT

A pair of spaced apart grooves are machined in a plate in correspondence with the movement of a patient's left and right condyles relative to the sockets in which they move. A third groove is also machined in the same plate, equally spaced and remote from the pair of grooves, in correspondence with the minimal separation of the patient's mandibular and maxillary teeth at various lateral and anterior positions. The plate is then attached to a cast of the patient's maxillary teeth and is mounted in an articulator frame on rigid posts which slide in the machined grooves of the plate as the plate is manually moved, thereby reproducing movements corresponding to the patient's closure pathway and condylar topography.

9 Claims, 9 Drawing Figures

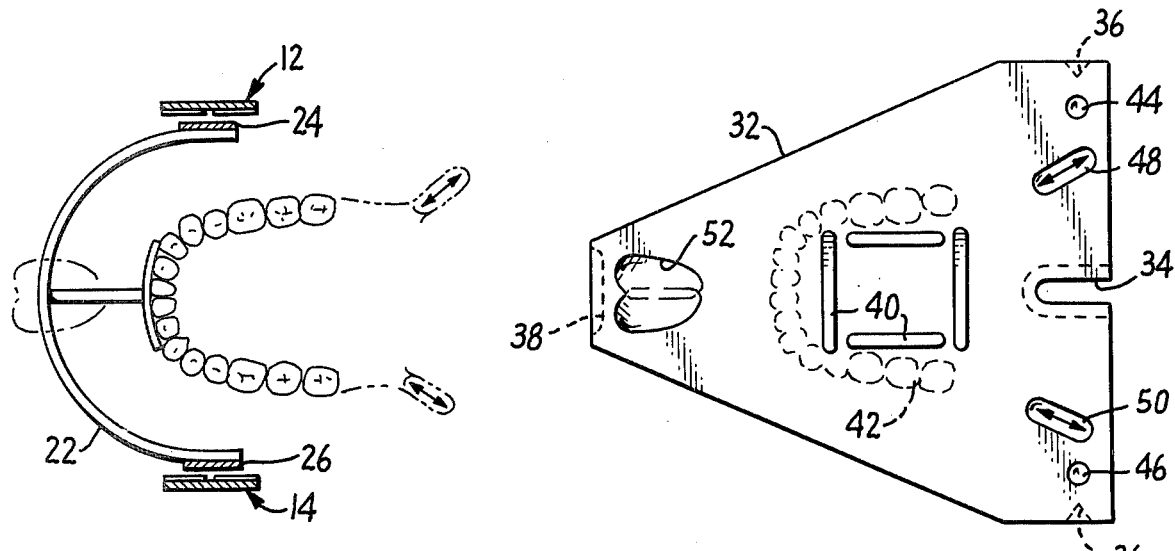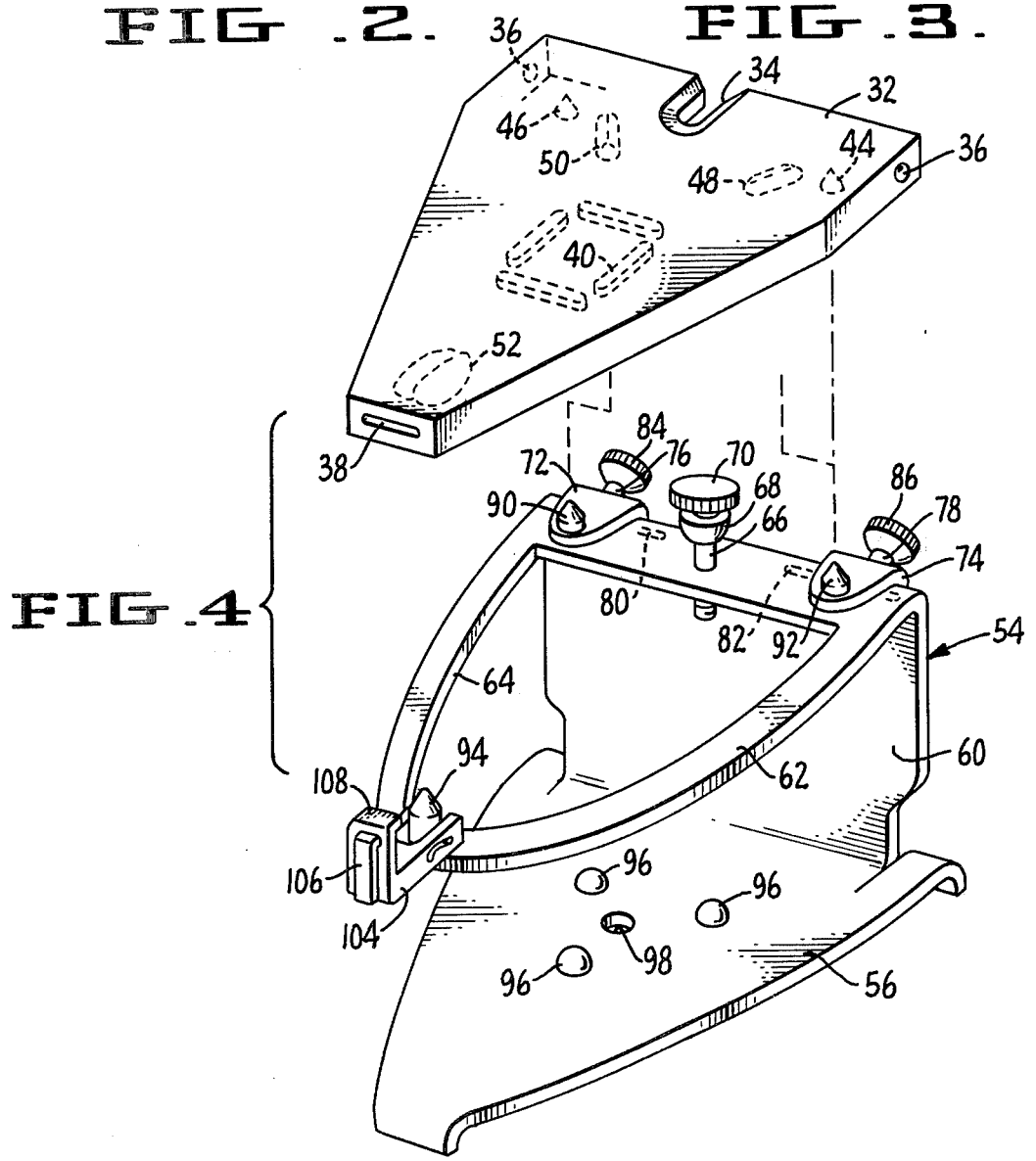

DEVICE FOR RECORDING AND REPRODUCING MANDIBULAR MOTION

BACKGROUND OF THE INVENTION

1. Field of the Invention

This invention relates to an improved dental articulator and more particularly to a device for recording and reproducing mandibular motion.

2. Background of the Invention

Geometric details describing the relative locations of the teeth, the areas and inclinations of their individual surfaces, and the positions of the surfaces making contact during "full" occlusion, relative to the hinging joint of the jaw, each affect the health of the teeth and of the hinge of the jaw, i.e., the "temporo-mandibular joint." These details are altered by growth, wear, disease, trauma, surgery, orthodontic treatment, treatment of caries, and by addition of fixed prosthodontic devices. Also, these details are totally changed by introduction of full dentures. In diagnosing and treating functional disorders arising from misalignment of the teeth or the hinging joint, or in guiding treatment of normal patients to avoid introducing functional disorders, dentists use a two-part technique.

First the positions of the maxillary and mandibular teeth relative to the cranially fixed sockets for the temporo-mandibular joints are recorded by making an impression of those teeth and by relating the impression to the socket through mechanical means attached to the impression and extending extra-orally to a position in proximity to the socket and joint; these mechanical means have markers and adjustments which allow those markers to be positioned so as to minimize translation during hinging maneuvers of the jaw.

Second, the mechanical means and the impression attached thereto are mounted on an articulator, which is a device providing means for simulating motions of the temporo-mandibular joint. The mechanical means and impression are used to locate casts of the patient's teeth in the same relative position to the hinge axis of the articulator as the actual teeth had to the hinge axis of the patient's temporo-mandibular joint. Motions and interactions of the casts of the patient's upper and lower teeth are then studied and altered by the dentist to optimize treatment.

Articulators offering varying degrees of simulation are well known but with all of these prior art devices, as the simulation becomes more complex to allow greater adjustability, the devices have a higher initial cost and require more time by the clinician to effect the adjustments. Moreover, since the basic articulator is used for a number of patients, it must be readjusted for each new simulation. In most prior art articulators, however, no effective way is provided by means of dials, indicators, or the like, for keeping a record of the adjustments necessary for a particular patient which is adequate to allow repeated mounting of the casts or transfer of the casts to an alternate articular or device without either requiring significant time for readjustment or without losing significant precision of alignment.

SUMMARY OF THE INVENTION

The above and other disadvantages of prior art methods and devices, including articulators, for simulating and studying mandibular motion are overcome by the present invention which comprises a machinable plate for supporting a maxillary cast of teeth, the plate is aligned in an anterior-posterior direction with the front and rear of the cast of teeth, the rear of the plate having a pair of cut-out pathways representing the motion pathways of a patient's left and right condyles and the front of the plate having a cut-out pathway representing the minimal separations of the patient's mandibular and maxillary teeth during a set of predetermined motions of the patient's jaw. To reproduce the patient's mandibular and occlusal signatures, the plate is carried in an articulator frame which has an arm for supporting a mandibulary cast of teeth, a pair of spaced apart first and second conical posts mounted on the frame for engagement in separate ones of the rear cut-out pathways of the plate to thereby provide a pair of hinge points for movement of the plate relative to the frame and a third conical post mounted on the frame supporting the first and second posts so as to engage the frontal pathway of the plate. A spring loaded knob mounted on a centering post exerts a force on the plate toward the tips of the posts at a location between the first, second and third posts. The manual, forced movement of the plate relative to the frame with the first, second and third posts traveling in their respective cut-out pathways in the plate will reproduce the patient's condylar (mandibular) and occlusal signatures.

In the preferred embodiment of the invention, the plate has the shape of an isosceles triangle with the pair of cut-out pathways being located adjacent its base and the third cut-out pathway being located adjacent the vertex opposite to the base. The plate also has a slot extending in from the base edge, with the slot being perpendicular to the base and being located between the pair of cut-out pathways.

As mentioned above, the plate is held in engagement with the posts by means of a spring loaded knob mounted on a centering post. This fourth centering post is mounted on the frame between the first and second posts and is spaced slightly toward the third post from the line intersecting the first and second posts. The rounded knob is mounted on the tip of the post and is spring loaded toward its base. When the post is received in the plate's slot, the plate becomes centered between the first and second posts and the spring loaded knob resiliently bears against the top of the plate along the slot edges to exert a force on the plate toward the tips of the first, second and third posts.

Sliders, which are adjustably mounted on the frame, carry the first and second posts. A pair of slots in the frame, one on each side of the fourth post, extend in a direction which is perpendicular to the plate slot's length. A pair of clamps, one for each slider, extend through the sliders and the frame slots to confine the paths of travel of the sliders to the frame slot lengths, and to selectively clamp the sliders to be immovable in the slots.

A locking clip is attached to the third post for selectively pressing the plate against the tip of the third post to lock the plate against movement relative to the third post.

It is therefore an object of the invention to provide an articulator which provides a permanent record of the patient's condylar and occlusal signatures.

It is another object of the invention to provide an articulator which is lower in initial cost.

It is yet another object of the invention to provide an articulator which requires minimal adjustment time by the clinician.

It is a further object of the invention to provide an articulator which allows more flexibility of the simulated motions.

It is a still further object of the invention to provide an articulator which provides more exact simulations of the mandibular motions.

It is yet a further object of the invention to provide an articulator which allows mounting of casts of the maxillary teeth without requiring dedication of expensive parts of the articulator during the mounting of the casts thereon.

It is still another object of the invention to provide apparatus which allows production of the articulator and of the devices for attaching the individual patient casts thereto with a precision that permits transfer of those casts from one articulator to another without error.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 2 is a horizontal, sectional view showing the patient's maxillary teeth and the maxillary transducer frame of the invention;

FIG. 3 is a planar view of the bottom of the recording plate of the invention;

FIG. 4 is an exploded, perspective view of the record plate and articulator of the invention;

DETAILED DESCRIPTION OF THE PREFERRED EMBODIMENTS

The important adjustments provided by articulators involve control of the topography of the sockets in which the condyles move, the separation of those sockets, the topography of the frontal surface controlling disengagement of the teeth and the relative positioning of those controlled elements and surfaces with the hinging axis of the mandible and with the maxillary teeth. The cost of providing adequate articulators as well as the difficulty in adjusting those articulators is intimately associated with those adjustments.

It is an important feature of the present invention that all or some of the variable features characterizing a patient's, or an idealized set, or partial set, of mandibular motion signatures, or a mixture thereof, be mechanically recorded on a single structure to which a cast of the patient's teeth is attached. This structure, when combined with an improved articulator frame according to the invention, allows the recorded mandibular motion signatures to be reproduced with respect to the cast of teeth.

Figure 1:
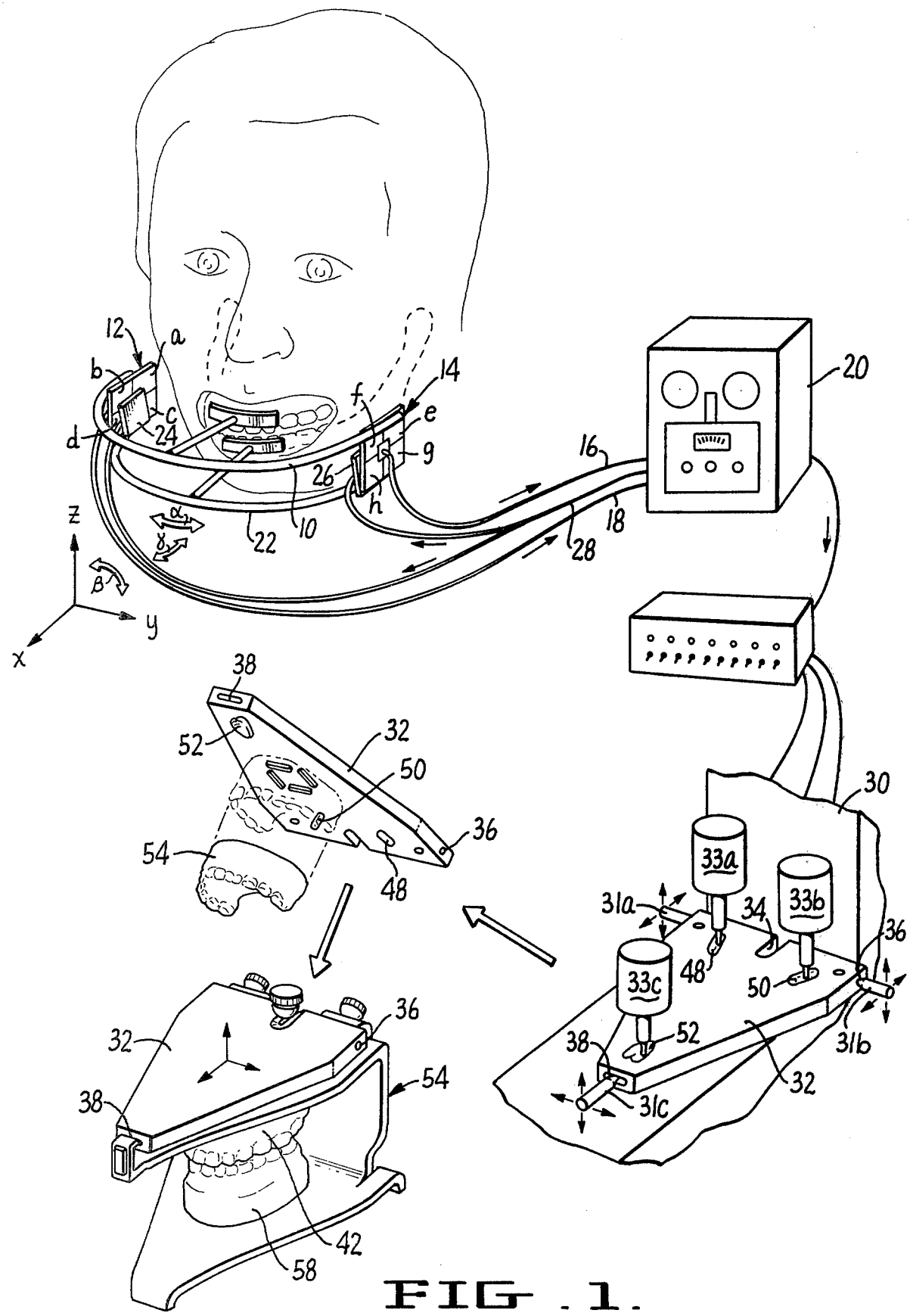
FIG. 1 is a diagram illustrating a system for producing the mandibular motion signature record plate according to the invention, together with the mechanism for reproducing the recorded information.

Referring now more particularly to FIG. 1, in order to measure the motion signatures of the patient's mandible and the occlusal pathway, a first arch-shaped structure 10 is attached to the patient's maxillary teeth. The arch-shaped frame 10 supports two opposed sets of sensing pads 12 and 14 on the right and left side of the patient's face, respectively. The sensing pad set 12 is made up of four sensing pads a, b, c and d; and the sensing pad set 14 is made up of sensing pads e, f, g and h. Individual pads of each set are separately connected through cables 16 and 18 to an electronic circuit 20.

A second arch-shaped frame 22 is attached to the mandibulary set of the patient's teeth and supports a pair of oscillator driven plates 24 and 26 on the right and left sides of the patient's face, which are roughly aligned in opposition to the pad sets 12 and 14, respectively. Plates 24 and 26 are connected by means of a cable 28 to the electronic circuit 20.

The electronic circuit 20 contains an electronic oscillator which supplies an alternating current to the plates 24 and 26. The pad sets 12 and 14 pick up the alternating current field on the plates 24 and 26 to varying degrees depending upon the extent to which the plates of the pad sets 12 and 14 overlap the areas of the plates 24 and 26 and upon the relative spacing between the plates 24 and 26, and the individual pad sectors a through h. The currents which are thus induced in the pads a through h are rectified in the electronic circuit 20 and are amplified by standard electronic means to produce quasi-steady state voltages $V_a$ through $V_h$, respectively, which are proportional thereto. The details of the electronic circuit 20 will not be described herein but are the subject of the applicant's co-pending patent application, Ser. No. 966,017, filed Dec. 4, 1978, and entitled NON-CONTACTING DEVICE FOR SENSING MULTI-COMPONENT MOTIONS. This co-pending application is incorporated herein by reference.

The six motions which characterize the arch-shaped structure 10 supporting pads a through h relative to the arch-shaped structure 22 supporting the driven plates 24 and 26 can be described in terms of the motions of a mid-point along a hypothetical axis which intersects all of the plates, that is, a hypothetical line passing between the intersection of the pads a through d, the plate 24, the plate 26 and the intersection of the pads e through h. These motions are a combination of three orthogonal linear motions X, Y, and Z, and three orthogonal angular motions $\alpha$, $\beta$, and $\gamma$. In terms of voltages, $V_a$ through $V_h$ derived from the sensing pads 12a through 14h, small motions can be expressed by the closely approximating equations:

$$X = l \cdot \left[ \frac{V_b + V_d + V_f + V_h - V_a - V_c - V_e - V_g}{V_a + V_b + V_c + V_d + V_e + V_f + V_g + V_h} \right]$$

$$Y = m \cdot \left[ \frac{V_a + V_b + V_c + V_d - V_e - V_f - V_g - V_h}{V_a + V_b + V_c + V_d + V_e + V_f + V_g + V_h} \right]$$

-continued $$Z = h \cdot \left[ \frac{V_a + V_b + V_e + V_f - V_c - V_d - V_g - V_h}{V_a + V_b + V_c + V_d + V_e + V_f + V_g + V_h} \right]$$

$$\alpha = \frac{l}{W} \left[ \frac{V_b + V_d - V_f - V_h - V_a - V_c + V_e + V_g}{V_a + V_b + V_c + V_d + V_e + V_f + V_g + V_h} \right]$$

$$\beta = \frac{h}{W} \left[ \frac{V_a + V_b - V_c - V_d - V_e - V_f + V_g + V_h}{V_a + V_b + V_c + V_d + V_e + V_f + V_g + V_h} \right]$$

$$\gamma = 2 \cdot \left[ \frac{hl \frac{V_b + V_c + V_f + V_g - V_a - V_d - V_e - V_h}{V_a + V_b + V_c + V_d + V_e + V_f + V_g + V_h} XY}{l^2 - h^2 + Y^2 - X^2} \right]$$

where
- l = the length of the plates 24 and 26;
- h = the height of the plates 24 and 26;
- m = the distance between the plates 24 and 26 and the sensing plates 12 and 14; and
- W = the distance between the plates 24 and 26.

In positioning the frames 10 and 22, the sensor axis, as determined by the hypothetical line mentioned above, is positioned to pass through the hinge axis of the jaw of the patient. If the right and left condyles of the patient lie at hypothetical points $X_{RO}$, $Y_{RO}$, and $Z_{RO}$ and at $X_{LO}$, $Y_{LO}$, and $Z_{LO}$, respectively, then the position of the displaced condyles ($X_{RD}$, $Y_{RD}$, $Z_{RD}$ and $X_{LD}$, $Y_{LD}$ and $Z_{LD}$) can be related to the positions of the centers of the plates 24 and 26, by noting that:

$$X_{RD} = X_{RO} + \left( \frac{2Y_{RO}}{W} \right)^\alpha$$

$$X_{LD} = X_{LO} + \left( \frac{2Y_{LO}}{W} \right)^\alpha$$

$$Z_{RD} = Z_{RO} + \left( \frac{2Y_{RO}}{W} \right)^\beta$$

$$Z_{LD} = Z_{LO} + \left( \frac{2Y_{LO}}{W} \right)^\beta$$

and that for small $\alpha$ and $\beta$, $$Y_{RD} \simeq Y_{LD} \simeq Y_{RO} + Y \simeq Y_{LO} + Y$$

Voltage signals proportional to these distances between the right and left condyles from their initial positions are generated by the circuit 20 and are supplied as control signals to the servo-controlled milling machine 30 which moves relative to servo-controlled milling tools 33a, 33b, 33c and a record plate 32 by separate motor driven means arranged to produce motions in the directions A, B, C, D, E and F through the various directions in a manner known, per se,* to duplicate the motion of the mandible relative to the cranial structure; the indexing points 31a, 31b and 31c having been previously positioned relative to plate 32 and machining means 33b, 33d and 33c so as to duplicate the relative positions of the plate 32 and the patient's right and left condyles and some pre-incisal point. The motor driven means A, B, C, D, E and F produce independent linear motions, each separate and independent motion being servo-controlled to reproduce measured motions derived from the mandible.

*See, for example, U.S. Pat. No. 4,111,085 and McGraw-Hill *Encyclopedia of Science and Technology*, Vol. 13, pages 692–699.

It is to be understood that the circuit 20 includes appropriate apparatus to reduce the transducer signals to recordable analog or digital form so that they can either be buffered in being supplied to the machine 30 or otherwise delayed to allow the machine sufficient time to carry out the cutting operation.

Referring now more particularly to FIG. 3, the machinable plate 32 is originally manufactured to have certain locating indentations and slots so that it may be accurately positioned in both the articulator frame to be described and in the milling device 30. Although the particular configuration for the plate is not especially important, the plate depicted in FIG. 3 does have the shape of an isosceles triangle. At the mid-point of the base of the triangle, the plate is provided with a slot 34 which extends generally perpendicular to the base edge of the plate. The slot edge on the opposite face of the plate from that shown in the figure is provided with a V-shaped bevel (shown in hidden line fashion in FIG. 3, and in full line fashion in FIG. 4). Separate conical depressions 36 are provided in the edge of each base corner of the plate. A V-shaped groove 38 is provided in the side of the plate at the vertex opposite to the base edge at the slot 34. The conical depressions 36 and V-shaped groove 38 are used to locate the plate 32 in an exact and repeatable position relative to other and related supporting structures such as the milling machine 30, as will be explained in great detail hereinafter.

A plurality of depressions 40, or alternatively, raised bosses, of more or less arbitrary shape and configuration is located in the center of the plate 32. As will be explained in greater detail hereinafter, these depressions are used to affix a plaster cast of the patient's maxillary set of teeth 42 to the plate and are for the purpose of providing gripping surfaces for the cement which attaches the cast to the plate.

In order for the plate 32 to act as a record of the patient's mandibular and occlusal pathway signatures, the signal supplied to the milling machine 30 by the circuit 20 causes the milling machine to cut out representative pathways in the base of the plate 32, which effectively represent these motion signatures. In operation, the set of transducers 12 and 14 carried by the arc frame 10 are intially adjusted to locate the hinge axis of the patient, the lateral distances between the patient's right and left condyles, and the mid-cranial sagittal planes. The plate 32 is placed in the jig of the servo-controlled milling machine 30 and the machine is operated so that cutting tools 33a and 33b cut a pair of conical depressions 44 and 46 which are each a measured and precisely-controlled distance from the center line of the slot 34. This distance is greater by a fixed and known amount than the measured distance of the patient's left and right condyles, respectively, from the sagittal point.

The milling machine cutting tools 33a and 33b are then retracted and moved inwardly toward the slot 34 to positions which are laterally displaced from the center line of the slot 34 by distances which are equal to the respective condylar separations from the sagittal plane. The cutting tool is then returned to the cutting position against the plate 32. Under control of the electronic circuit 20, the motor drive means A, B, C, D, E and F move plate 32 so that the cutting tools 33a and 33b cut separate pathways 48 and 50 on opposite sides of the slot 34 as the patient moves his or her jaw through a predetermined set of maneuvers. This effectively records information characterizing the right and left condylar motion patterns of the patient in the form of the contoured depressions 48 and 50, respectively.

Simultaneously, with this procedure, a separate cutting means 33c is located so as to cut a similar depression 52 on the surface of the plate 32 near the groove 38, to duplicate the motion of a point which is mechanically fixed to the mandible and located a fixed distance anterior of the condylar hinge axis along a line which is perpendicular to that axis, intersecting that axis at the mid-cranial point, and contained in a plane which also contains a point of convenient reference on the patient. Such a point of reference might be, for example, a small tatoo mark near the right nostril. This mark, of course, is placed on the patient for convenient reference in subsequent treatment. This cutting tool produces the cut-out pathway 52 which records the minimal separations of the mandibular and maxillary teeth at various lateral and anterior positions.

A first important objective of the invention is thus met by producing the plate 32 and the cut-out pathways 48, 50 and 52. These combined pathways, produced during a set of established and controlled maneuvers of the patient's mandible form a permanent record of the patient-generated closure pathways and condylar socket topography. This record is useful and desirable as a diagnostic tool, as a medical record, and as a legal record.

Figure 9:
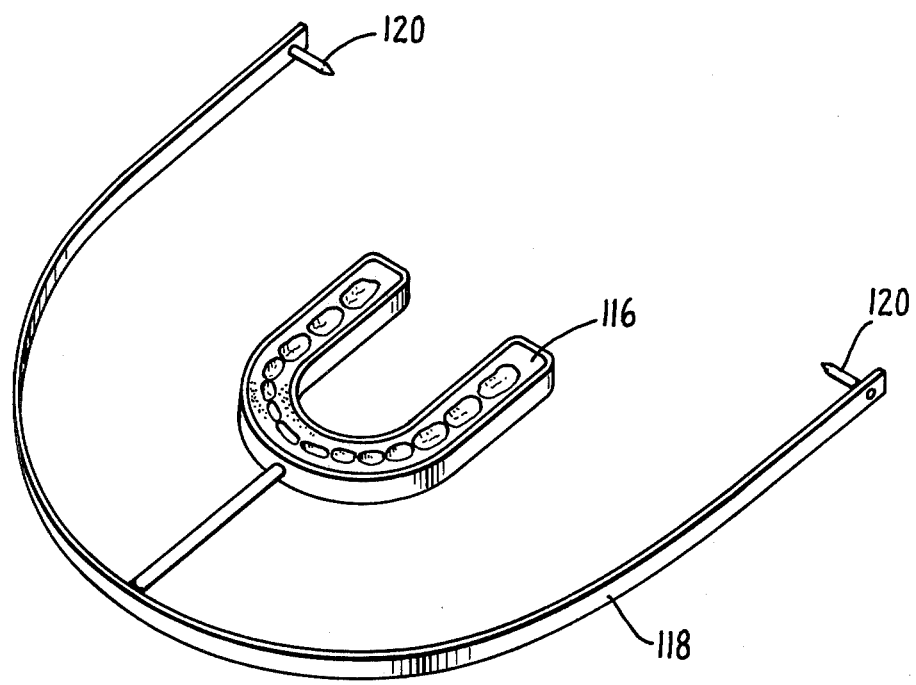
FIG. 9 is a perspective view of a wax impression bite plate and its locating frame.

Referring now more particularly to FIGS. 1, 4 and 9 a second objective of the invention will be discussed, namely, the use of the plate 32 as an integral part of an articulator of simplified design and improved performance. To accomplish this objective, wax impressions of the patient's maxillary and mandibular teeth are taken in the usual fashion by means of a wax bite plate 116 mounted on an arc-shaped frome 118; which is similar to the transducer frames 10 and 22. The frame 118 has hinge locator points 120 which are aligned with the patient's hinge axis before the impressions are taken.

The frame 118 is then aligned with the plate 32 by placing the locator points 120 in the conical depressions 36 and a protrusion (not shown in FIG. 9) in the notch 38. The cast is then positioned relative to the wax impression and is cemented to the depressions 40 on the plate by standard techniques. In this way, the teeth cast is properly located relative to the cut-out pathways 48 through 52.

The plate 32 is then mounted in an articulator frame 54, which is best shown in FIG. 4. The manner in which the plate 32 is aligned in the frame 54 will be described in greater detail hereinafter; however, it is first necessary to understand the particular construction of the articulator frame 54.

Referring now more particularly to FIG. 4, the articulator frame 54 has a base arm 56 suitable for carrying a cast 58 (see FIG. 1) of the patient's mandibular teeth. The base portion 56 is generally in the shape of an isosceles triangle, although in other embodiments it could have other shapes. A flange portion 60 is attached along the base edge of the portion 56 at right angles to it. A third portion of the frame is attached at the opposite edge of the flange 60 from the base 56 and extends perpendicularly from the flange 60 and parallel to the base portion 56. Thus, the upper arm portion 62 overlies the base arm 56 and is parallel to it.

The upper arm 62 contains a cut-out which has generally the same configuration as the plate 32 but is smaller in area, so that the plate 32 cannot pass through the cut-out 64 when laid on top of the upper arm 62.

Figure 5:
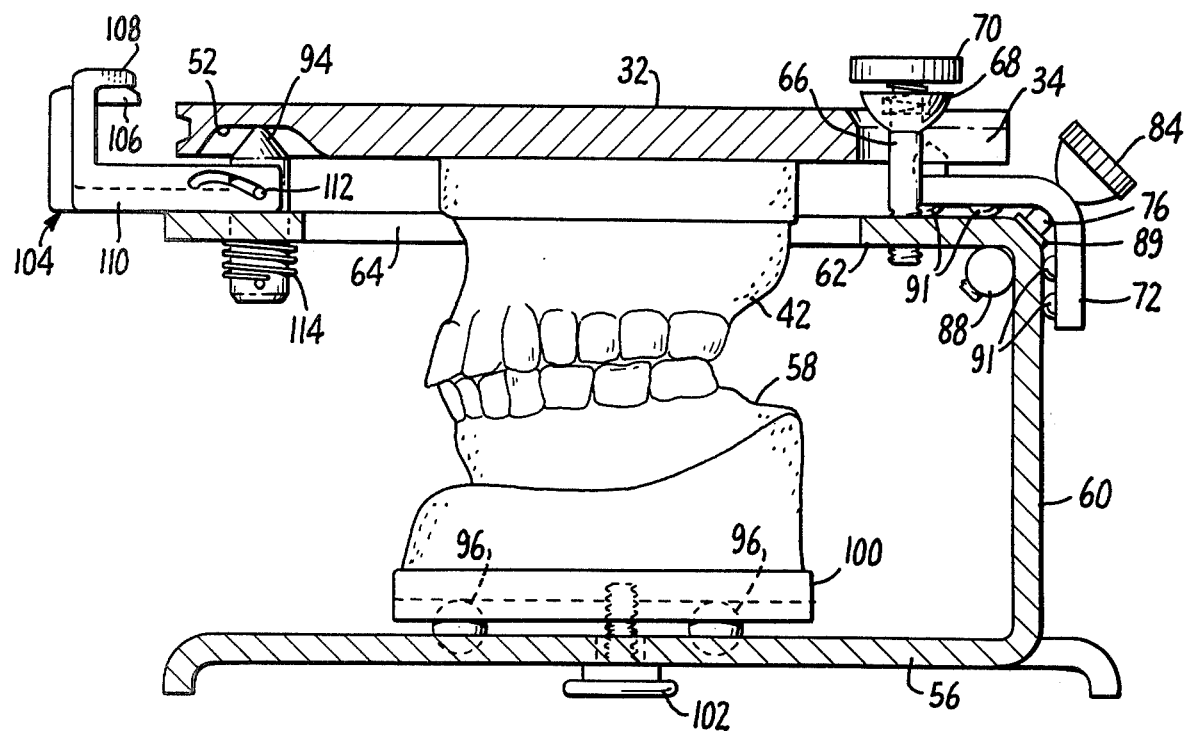
FIG. 5 is a vertical view, partly in section, of the record plate and articulator of the invention assembled for use.
Figure 6:
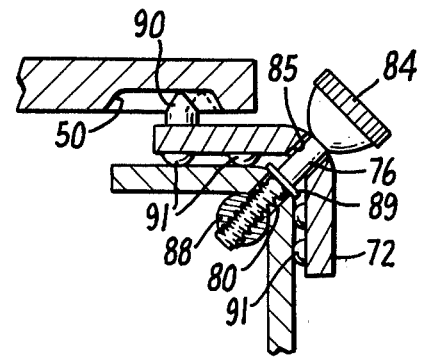
FIG. 6 is a vertical, sectional view of a slider clamp mechanism of the articulator depicted in FIG. 5.

A centering post 66 is provided with threads which are engaged in a hole in the upper arm 62 of the frame 54 at a point which is located mid-way along the base edge of the upper arm 62, and set in from the base edge towards the cut-out portion 64. The centering post 66 has a spring loaded spherical collar 68 and a thumb screw knob 70. The collar 68 is biased away from the knob 70 towards the upper arm 62. A pair of right angle-formed sliders 72 and 74 are positioned on opposite sides of the centering post 66 and slide along the corner junction of the flange 60 with the top arm 62. The sliders are held in place by means of separate posts 76 and 78 which pass through the sliders and through separate slots 80 and 82 along the junction of the flange 60 with the top arm 62. The outer ends of the posts 76 and 78 have spherically bottomed spring-loaded thumb screw knobs 84 and 86 which resiliently bear against the sliders. The other ends of the posts 76 and 78 are threaded into separate cylindrical or spherical nuts 88 which slide along the inner corner of the junction of the flange 60 with the top arm 62, as best viewed in FIGS. 5 and 6. The posts have annular shoulders 89. Thus, the limit of travel of each of the sliders is the length of the respective slots 80 and 82.

Each of the sliders 72 and 74 carries a separate, conically-tipped post 90 and 92 which project upwardly above the frame portion 62. The sliders contact the flange 60 and top arm 62 through five captured balls 92 mounted on the sliders. Each of the sliders is also provided with a slot 85 (See FIG. 6) corresponding to the slots 80 and 82, respectively. Each end of the slots 85 is provided with a detent (not shown) to provide preset stops for the positions of the sliders corresponding to the distance between the depressions 44, 46 and the pathways 48 and 50, respectively. In the operation of the frame, the sliders 72 and 74 are moved under posts 76 and 78 in directions outwardly disposed from post 70 until the inwardly disposed detents on the sliders are engaged by the spherically bottomed, spring-loaded thumb screw knobs 84 and 86 respectively. The plate 32 is then laid on top of the upper arm 62 with the slot 34 straddling the center post 66. The sliders are then moved laterally with the posts 90 and 92 are engaged in the conical depressions 46 and 44. The thumb knobs 84 and 86 are then turned to tighten down the shoulders 89 against the flange 60 and thereby lock the posts 76 and 78 in a rigid relationship with the flange 60.

After the initial adjustment process as described above, the sliders 72 and 74 are repositioned toward the centering post 66 until the spring loaded knobs 84 and 86 seat in the detents at the inner ends of the slots 85 which is the precise distance necessary to place the posts 90 and 92 at the proper position within the cut-out pathways 50 and 48, respectively. The front portion of the plate 32 is then lowered to allow the depression 52 to rest on top of a third conical post 94 which is more or less equally spaced from the posts 90 and 92 on the opposite side of the cut-out 64 of the upper arm 62. Together the post 66 and the post 94 lie along a hypothetical axis of bilateral symmetry of the plate 32. The post 66 is closer to the post 94, as well as to the cut-out portion 64, than the posts 90 and 92.

The posts 90 and 92 establish a hinging axis for the plate 32 relative to the upper arm 62. Because of the spring loaded spherical collar 68 on the post 66, a slight force is maintained against the plate 32 to cause it to hinge about the posts 90 and 92 and to hold the plate so that the posts 90, 92 and 94 engage in the respective cut-out portions 50, 48 and 52 of the plate 32. These three points of engagement between the plate 32 and the frame 54 allow the plate 32 to be moved relative to the frame 54 within the limits defined by the contours of the cut-out portions 48, 50 and 52. These limited motions reproduce the motions of the patient's mandible which occurred during the generation of the cut-out portions as described above.

In order to locate the maxillary cast 58 with respect to the base portion 56, the base portion 56 is provided with a plurality of captured balls 96 in a triangular configuration centered about a hole 98 in the base portion 56, i.e., the balls 96 lie on hypothetical rays spaced 120° apart emanating from the hole 98. As best viewed in FIG. 5, the mandibulary cast 58 is mounted on a base plate 100, in a manner to be described hereinafter, which has three V-shaped grooves (not shown) on its bottom surface which radiate outwardly from a center hole (not shown) at 120° angles. This hole receives a threaded screw 102 which passes through the hole 98 and clamps the plate 100 against the base portion 56 while the balls 96 track in the V-grooves of the plate to accurately position the plate with respect to the frame 54 in a repeatable manner.

A plate locking mechanism 104 is provided adjacent the front post 94. The locking mechanism 104, as best viewed in FIGS. 4 and 5, contains a center hook portion 106 and an upper clip portion 108, each of which rides over the top forward edge of the plate 32 when pushed towards the centering post 66. The locking portion 108 has a pair of forked arms 110, which straddle the post 94, and which capture an outwardly extending pin 112 from the post 94. This pin 112 rides in slots in the fork arms 110 which slots are configured so as to raise the post 94 against the action of a coil spring 114 and to cause the post 94 to fully engage in the cut-out portion 52 and to press the plate 32 upwardly against the clip 108. It should be noted here that the hook 106 and the clip 108 are independently movable and provide alternate means for locking the plate 32 with respect to the upper arm 62.

In order to cement the cast of the patient's mandibular teeth to the plate 100, the hook 106 is pushed forwardly to engage the top of the plate 32, and to hold it and the maxillary cast 42 in a fixed position relative to the post 94. The sliders 72 and 74 are next positioned at the outwardly located detent positions so that the post 90 and 92 are engaged in the conical depressions 46 and 44, respectively. After placing the maxillary wax impression of the bite plate 116 against and aligned with the corresponding surfaces of the maxillary cast 42 the mandibular cast 58 is aligned with the wax impression of the mandibular teeth on bite plate 116 and cemented to plate 100. After the cast 58 has been firmly cemented to the plate 100, the assembled articulator and cast can be prepared for storage as a unit by sliding forward the alternate clamping piece 108, toward the centering post 66, to engage the pin 112 in the post 94 and thereby raise it upwardly into the cut-out 52 against the force of the spring 114, whereby the plate 32 is raised to disengage the maxillary cast 42 from the mandibular cast 58.

The use of the articulator frame 54 together with the plate 32 to simulate the patient's mandibular and occlusal signatures, proceeds in the usual manner. One significant difference, however, it that the plate 32 together with the maxillary cast 42, as well as the mandibular cast 58 and the plate 100, can be transferred to another articulator frame 54 without error, provided only that the conical tips of posts 90 and 92 accurately located with respect to the balls 96.

Figure 7:
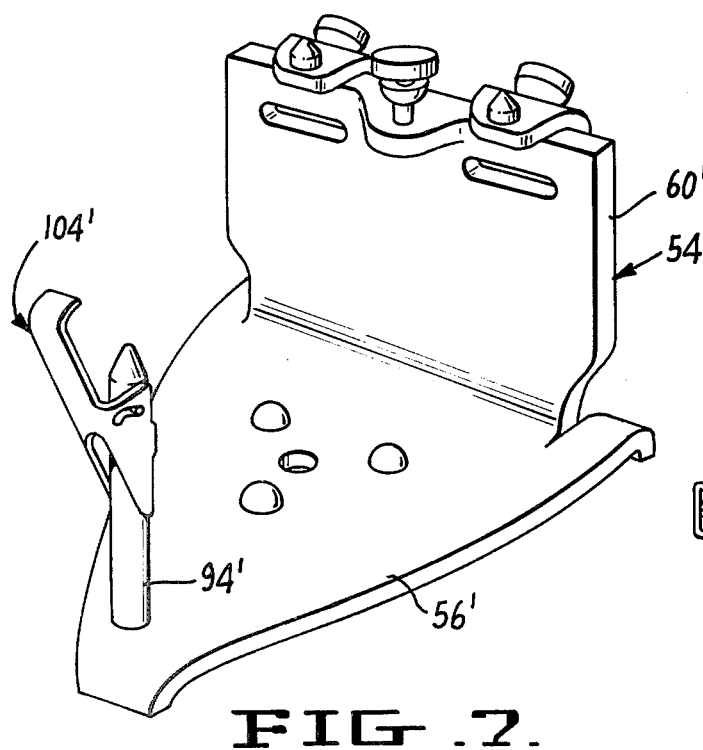
FIG. 7 is a perspective view of an articulator of a second embodiment of the invention.

Referring now more particularly to FIG. 7, an alternative embodiment of the articulator frame 54' is displayed. In this modified embodiment, the upper arm 62 is omitted and sliders 72' and 74' are mounted simply on an upstanding flange 60' connected to a base 56'. A frontal post 94' is projected directly upward from the base 56' and has a locking mechanism 104' which is pivoted to the post 94' and which raises the conical tip by the same mechanism as described above in reference to FIG. 5.

Figure 8:
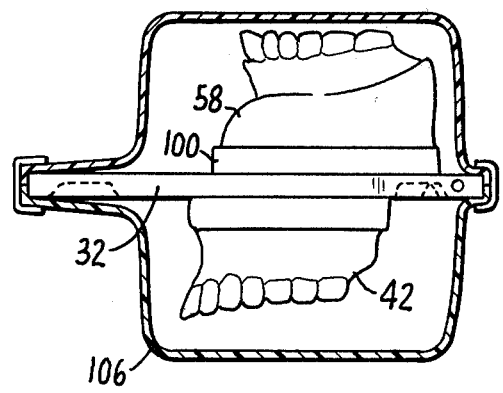
FIG. 8 is a vertical view, partly in section, of the record plate and cast teeth mounted in a case for storage or shipment.

Referring now more particularly to FIG. 8, the plate 32, together with the maxillary cast 42, is mounted in a plastic case 106 for storage and shipment. The mandibulary cast 58 and plate 100 are stored on top of the plate 32 within the protective cover 106.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention claimed.

What is claimed is:

1. Apparatus for providing a reproducible record of the mandibular motion of a patient, comprising
   a machinable plate for supporting a maxillary cast of teeth, the plate having a front and a rear, the rear of the plate having a pair of first and second cut-out pathways representing the motion pathways of a patient's left and right condyles and the front of the plate having a third cut-out pathway representing the minimal separations of the patient's mandibular and maxillary teeth, during a set of predetermined motions of the patient's jaw,
   an articulator frame, including an arm for supporting a mandibulary cast of teeth, a pair of spaced apart first and second conical posts mounted on the frame for engagement in separate ones of the first and second cut-out pathways of the plate to provide thereby a pair of hinge points for movement of the plate relative to the frame and a third conical post mounted on the frame for selective engagement with the third cut-out pathway of the plate, and
   resilient means for exerting a force on the plate towards the tips of the posts, at a location between the first, second and third posts, whereby manual, forced movement of the plate relative to the frame with the first, second and third posts traveling in their respective cut-out pathways in the plate simulates motions of the patient's mandible.

2. Apparatus for providing a mandibulary record as recited in claim 1, wherein the plate has the shape of an isosceles triangle with the pair of cut-out pathways being located adjacent its base edge and the third cut-out pathway being located adjacent the vertex edge opposite the base.

3. Apparatus for providing a mandibulary record as recited in claim 1, wherein the plate has a slot perpendicularly extending in from the rear and being located midway between the pair of cut-out pathways.

4. Apparatus for providing a mandibulary record as recited in claim 3, wherein the resilient means comprise a fourth post mounted on the frame at a location which is midway between the first and second posts and is spaced closer to the third post than are the first and second posts, and a rounded knob which is slidably mounted on the tip of the post and is spring loaded toward the base of the post, whereby when the post is received in the plate's slot, the plate becomes centered between the first and second posts and the spring loaded knob resiliently bears against the top of the plate along the slot edges to exert a force on the plate towards the tips of the first, second and third posts.

5. Apparatus for providing a mandibulary record as recited in claim 4, wherein the frame has a pair of slots, one on each side of the fourth post, which extend in a direction which is perpendicular to the plate slot's length, and further comprising slider means which are adjustably mounted on the frame for carrying the first and second posts, the slider means including a pair of sliders, each of which carries one of the first or the second posts, a pair of clamps, one for each slider, which extend through the sliders and the frame slots to confine the paths of travel of the sliders to the frame slot lengths.

6. Apparatus for providing a mandibulary record as recited in claim 5, wherein the plate has a pair of conical depressions which are aligned with the first and second cut-out pathways and wherein the sliders are each movable between a first position in which the posts carried by the sliders are aligned with the plate for engagement in the respective conical depressions to initially orient the plate with respect to the frame and a second position wherein the posts carried by the sliders are aligned for engagement in separate ones of the first and second cut-out pathways.

7. Apparatus for providing a mandibulary record as recited in claim 1, further comprising locking means attached to the third post for selectively pressing the plate against the tip of the third post to lock the plate against movement relative to the third post.

8. Dental apparatus for mechanically recording the mandibular and occlusal signatures of a patient, comprising
transducer means connected between the patient's mandible and the cranial structure for producing separate electrical signals representative of relative motion at selected locations between the mandible and the cranium along and about three orthogonal axes; the transducer means being initially aligned with the hinge axis of the patient's mandible,
a machinable plate for mounting a maxillary cast of teeth,
servo-controlled cutting tool means for cutting pathways in the plate, the servo-controlled cutting tool being connected to the transducer means and controlled by the electrical signals produced thereby so as to cut pathways in the plate having configurations which are representative of the relative motion at selected locations between the patient's mandible and the cranium.

9. Dental apparatus as recited in claim 8, wherein the transducer means comprise a first plate and a second plate, the second plate being divided into a plurality of electrically insulated sensing pads, support means for attaching one of the first and second plates to the patient's maxillary teeth and the other of the first and second plates to the patient's mandibulary teeth so that the plates are parallel to each other but spaced apart, oscillator means for applying an alternating current signal between the plates, and means for detecting variations in the capacitive charge on the sensing pads caused by relative movement between the first and second plates and for producing the electrical signals representative of the relative motions between the first and second plates along and about three orthogonal axes.

* * * * *